(12) United States Patent
Kurtz et al.

(10) Patent No.: US 11,602,334 B2
(45) Date of Patent: Mar. 14, 2023

(54) SYSTEM AND METHOD FOR CONTACTLESS MONITORING OF CO2 IN NEONATALS

(71) Applicant: Oridion Medical 1987 Ltd., Jerusalem (IL)

(72) Inventors: Azriel Kurtz, Maale Adumim (IL); Konstantin Goulitski, Holon (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 450 days.

(21) Appl. No.: 16/737,016

(22) Filed: Jan. 8, 2020

(65) Prior Publication Data

US 2020/0222031 A1   Jul. 16, 2020

Related U.S. Application Data

(60) Provisional application No. 62/792,438, filed on Jan. 15, 2019.

(51) Int. Cl.

| | |
|---|---|
| *A61B 10/00* | (2006.01) |
| *G01N 33/497* | (2006.01) |
| *A61G 11/00* | (2006.01) |
| *A61B 5/083* | (2006.01) |
| *A61B 5/00* | (2006.01) |

(52) U.S. Cl.
CPC ............ *A61B 10/00* (2013.01); *A61B 5/0836* (2013.01); *A61B 5/6892* (2013.01); *A61B 5/706* (2013.01); *A61G 11/00* (2013.01); *G01N 33/497* (2013.01); *A61B 2010/0087* (2013.01); *A61B 2503/045* (2013.01); *A61B 2560/0223* (2013.01); *A61G 2203/30* (2013.01)

(58) Field of Classification Search
None
See application file for complete search history.

(56) References Cited

U.S. PATENT DOCUMENTS

| | | | |
|---|---|---|---|
| 4,885,918 A | * 12/1989 | Vaccaro | A61G 11/002 187/269 |
| 10,314,515 B2 | 6/2019 | Colman et al. | |
| 2018/0110077 A1 | * 4/2018 | Mandapaka | H04L 63/08 |
| 2018/0199731 A1 | * 7/2018 | Starr | A47D 15/001 |
| 2021/0030607 A1 | * 2/2021 | Scott | A47C 27/088 |

FOREIGN PATENT DOCUMENTS

JP        11137618 A   * 5/1999

* cited by examiner

*Primary Examiner* — Jay B Shah
(74) *Attorney, Agent, or Firm* — Cantor Colburn LLP

(57) ABSTRACT

A system for contactless monitoring of gas levels within an incubator, the system comprising at least one gas sampling line having a proximal end exposed to the internal space of the incubator, and a distal end associated with a monitoring unit for receiving a gas sample obtained from the incubator via the proximal end.

18 Claims, 7 Drawing Sheets

SYSTEM AND METHOD FOR CONTACTLESS MONITORING OF CO2 IN NEONATALS

CROSS-REFERENCE TO RELATED APPLICATIONS

This application claims priority to U.S. Provisional Patent Application Ser. No. 62/792,438 filed Jan. 15, 2019, the entire contents of which are incorporated herein by reference.

FIELD

The present invention is in the field of patient monitoring, in particular, monitoring of respiratory gases in neonatals.

BACKGROUND

It is common for many babies (also referred herein as neonatals), either having been prematurely born or having otherwise medical problems or conditions to be put under observation immediately or soon after birth. This is most commonly performed by placing the neonatal within an incubator or other isolated space, allowing to keep the baby under monitored conditions while receiving any desired treatment.

While in the incubator, the neonatal is subject to tests and its conditions are constantly monitored, as well as a variety of medical parameters such as blood pressure, blood saturation levels, respiratory functions etc.

It is also known to monitor $CO_2$ levels in neonatals using a variety of devices such as masks, nasal prongs and the like.

Acknowledgement of the above references herein is not to be inferred as meaning that these are in any way relevant to the patentability of the presently disclosed subject matter.

SUMMARY

In accordance with one aspect of this disclosure there is provided a system for contactless monitoring of gas levels within an incubator, the system comprising at least one gas sampling line having a proximal end exposed to the internal space of the incubator, and a distal end associated with a monitoring unit for receiving a gas sample obtained from the incubator via the proximal end.

In particular, the system can be configured for monitoring levels of respiratory gases of a neonatal located within the incubator, without the need to fit the neonatal with a mask, tube or any other mountable/wearable device. In accordance with a specific example, one of said respiratory gases may be $CO_2$.

The proximal end of the channel may be exposed to the internal space of the incubator and located within the incubator at a location reducing the likelihood of the proximal end being blocked either by the neonatal or by any equipment and/or objects within the incubator.

In addition, the system may comprise a plurality of sampling channels having their respective proximal ends arranged in different locations within the incubator, and configured for obtaining gas samples from different locations within the incubator.

Under the above arrangement, the distal ends of the channels may be connected by any one of the following configurations:
 a. each distal end is connected to an independent monitoring unit;
 b. two or more distal ends may be connected to the same monitoring unit; and
 c. any combination of (a) and (b).

When two or more of the distal ends are connected to the same monitoring unit, the monitoring unit may be fitted with a multi-channel processor configured for obtaining samples from a plurality of channels and analyzing them together to output a combined result.

In accordance with a particular example of the present invention, the system can comprise a plurality of sampling channels passing through a mattress located within the incubator and having their proximal openings exposed to the internal space of the incubator at the elevation level of the neonatal. In particular, it was shown that monitoring $CO_2$ levels at the elevation level of the infant (e.g. in close proximity to the surface/mattress on which the neonatal is positioned) yields significantly better results than in other heights within the incubator.

In addition, the arrangement may include spreading the proximal openings of the sampling channels across an area of the mattress of the incubator, thereby forming a sampling array. The sampling array may be particularly beneficial since the neonatal keeps moving and displacing within the incubator during its stay there. The sampling array thus elegantly provides a solution for uniform monitoring of $CO_2$, regardless of the location of the neonatal's head (and particularly mouth).

When using a sampling array, the system may be calibrated to identify the location from which sampling port each of the gas samples is obtained, thereby allowing it to form a special/areal map of the $CO_2$ samples and sample gradients, allowing to more accurately analyze and monitor said samples.

In addition, implementing a sampling array within the incubator also allows continuous sampling, even when some of the proximal openings of the array are blocked by the neonatal or by other equipment positioned within the incubator.

In accordance with a particular arrangement, the array may be distributed circumferentially around the approximated position of the head of the neonatal when placed on the support surface. Moreover, since neonatals, especially ones placed in incubators, are relatively immobile, the array may also have visual markings configured for indicating to the medical staff where to position the neonatal. For example, the array may be distributed in a circle-like manner, or a part thereof, and the head of the neonatal should be placed at the center of said circle. Thus, the array can be configured for obtaining samples on all sides of the neonatal's head.

In accordance with another example of the subject matter of the present application the system may comprise a support surface installed above the bottom of the incubator, the support surface configured for functioning as a mattress for the neonatal.

The support surface may be elevated above the bottom of the incubator forming a space sufficient for placing monitoring equipment. In addition, the support surface may be perforated (e.g. a net), allowing sampling of $CO_2$ therethrough, without the need for forming holes/channels in a mattress of the incubator.

In accordance with another aspect of the subject matter of the present application, there is provided a mattress configured for receiving therethrough a plurality of sampling channels of the monitoring system of the first aspect of the present application.

In accordance with yet another aspect of the present application, there is provided a method for retrofitting an incubator with the monitoring system of the first aspect of the invention, said method comprising the steps of:

forming one or more apertures within a mattress or wall of the incubator;

passing one or more sampling channels through said one or more apertures such that the proximal end is located at the level of the mattress; and connecting the distal end of the sampling channel to a monitoring unit configured for monitoring $CO_2$ levels.

Under the above aspect of the present invention, any neonatal incubator may be fitted with the monitoring system, allowing for more efficient monitoring in neonatals, which requiring no significant modifications to the incubator.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Figure 1A:
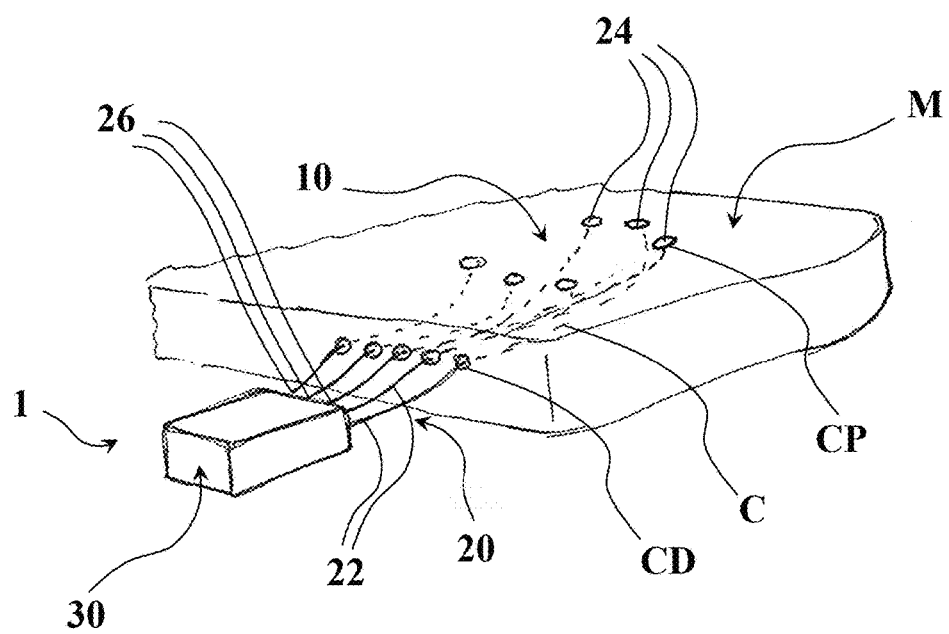
FIG. 1A is a schematic isometric view of an incubator mattress fitted with a sampling system according to the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION

Figure 1B:
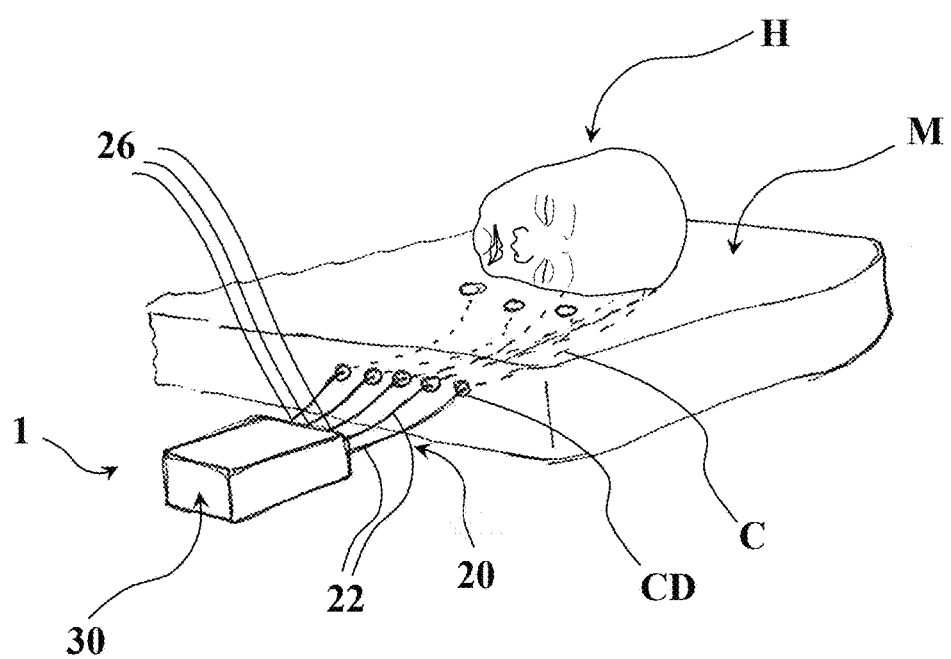
FIG. 1B is a schematic isometric view of the mattress shown in FIG. 1A, with a reference to the head of a neonatal to be positioned on the mattress.
Figure 1C:
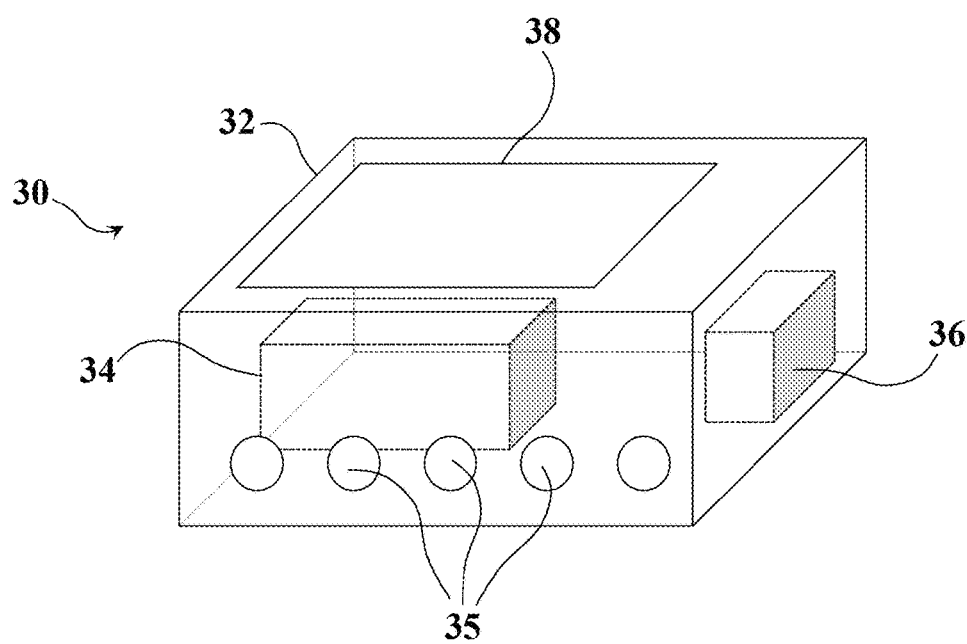
FIG. 1C is a schematic view of the monitoring system shown in FIGS. 1A and 1B.

Attention is first drawn to FIGS. 1A and 1C, in which an incubator mattress is shown, generally designated M and configured for being placed within an incubator. The mattress M a sampling system generally designated 1 and comprising a sampling arrangement 10 and a monitoring unit 30. The sampling arrangement 10 comprises a plurality of sampling channels 20, each constituted by a tube 22 having a proximal end 24 configured for obtaining a sample, and a distal end 26 associated with the monitoring unit 30 and configured for delivering the obtained sample thereto. The tubes 22 pass through corresponding cavities in the mattress M.

The monitoring unit 30 comprises a housing 32 with a plurality of ports 35, the housing 32 accommodating therein a power source 34, a processor 36 and a display 38. It should be noted that in some examples (not shown), the monitoring device may be connected to an external power source (electricity) and thus may not require an internal power source.

With additional attention being drawn to FIG. 1B, the mattress M is shown comprising a plurality of channel cavities C formed therein and configured for accommodating therethrough a corresponding plurality of the sampling tubes 20. The channels C are formed within the mattress having a proximal end CP open to the top surface of the mattress M on which the infant is to be positioned, and a distal end CD, allowing the tubes 20 to connect to the ports 35 of the monitoring device 30.

It is noted that the proximal ends CP in the mattress form an array surrounding locations at which the head of the infant is expected to be positioned during his stay within the incubator, thereby ensuring proper measurement of the infant's breath while lying on the mattress, regardless of his position.

Measurements taken by the different sampling points can be used to form a gradient map of the respiratory gasses around the head of the infant, thereby allowing achieving a more precise reading.

Figure 2:
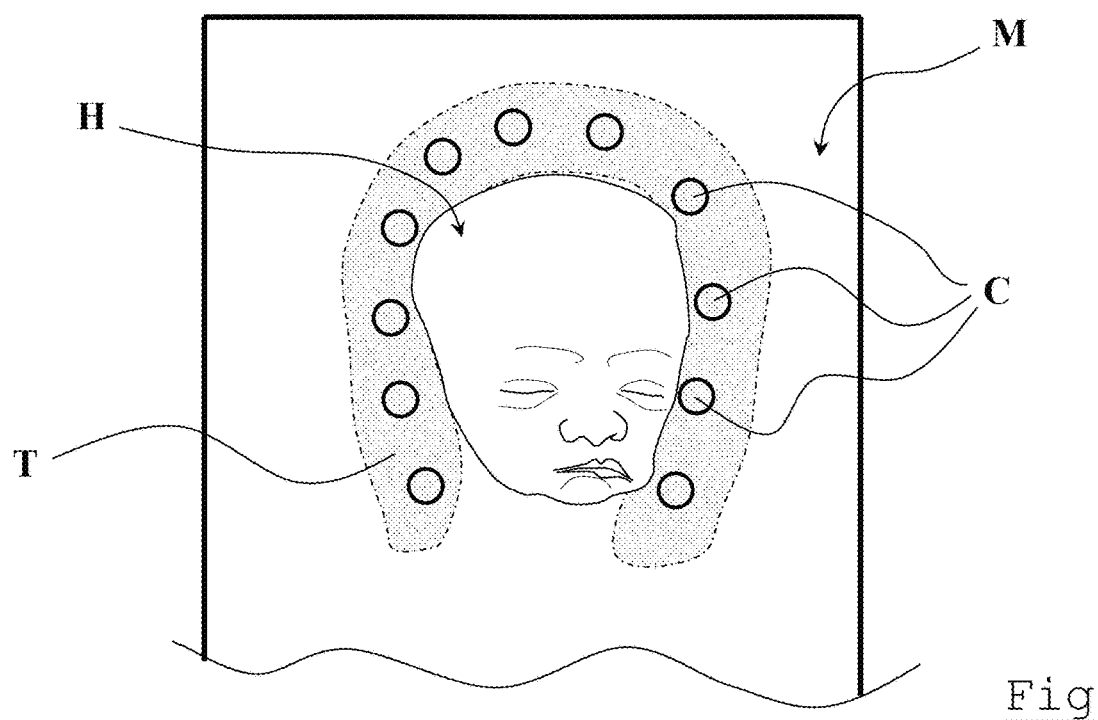
FIG. 2 is a schematic top view of a mattress similar to that shown in FIG. 2B, showing the spread of sampling points.

With additional reference being made to FIG. 2, the mattress M may have thereon an area T marking to the medical operator where to place the neonatal, this area T including therein the sampling ports 24. It should be noted that marking the area T (e.g. with a different color, texture etc.) visible to the medical operator provides a clear indication of the desired position of the neonatal, thereby reducing the risk of the infant's head obstructing any of the sampling ports 24.

Figure 3:
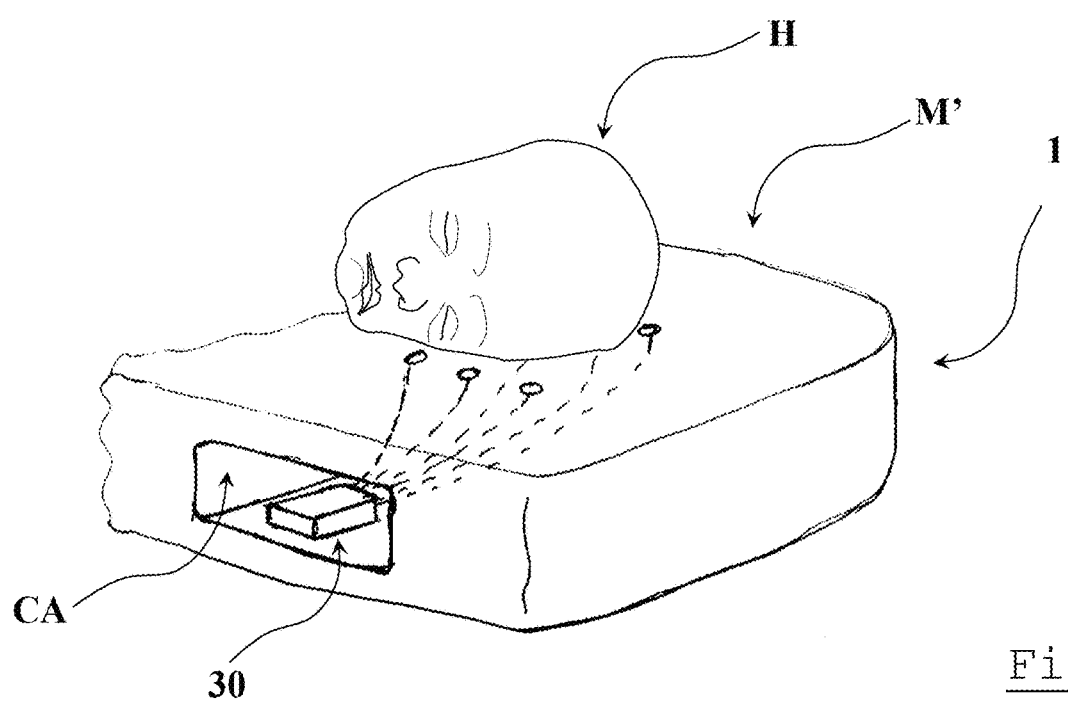
FIG. 3 is a schematic isometric view of an incubator mattress comprising a monitoring system according to another example of the present invention, with a reference to the head of a neonatal to be positioned on the mattress.

Turning now to FIG. 3, another example is shown in which the mattress M' is shown to be formed with a cavity CA configured for accommodating therein the monitoring device 30, wherein the entire mattress M' constitutes a self-contained monitoring system 1, which may be provided as a single module to constitute and add-on to an existing incubator.

Figure 4:
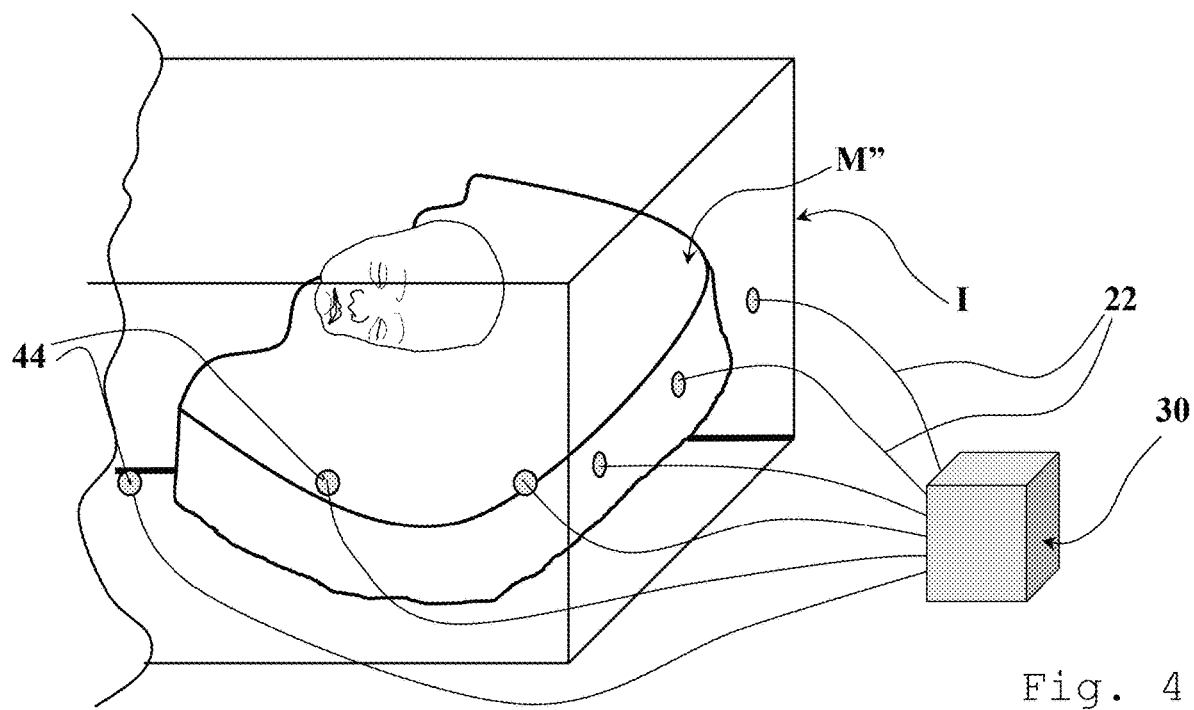
FIG. 4 is a schematic isometric view of an incubator and sampling system according to another example of the present invention.

With attention being drawn to FIG. 4, another example of the present invention is shown in which the sampling ports 44 are formed in the wall of the incubator I, rather than in the mattress itself. Under this arrangement, the sampling ports 44 still form an array around the neonatal's head but are free of the risk of being obstructed and do not come into contact with the neonatal at all.

It is noted that under this example as well, no channels are required to be formed and the tubes 20 are simply passed from the ports 44 directly to the monitoring device 30, allowing contactless sampling of the air within the incubator I.

Figure 5:
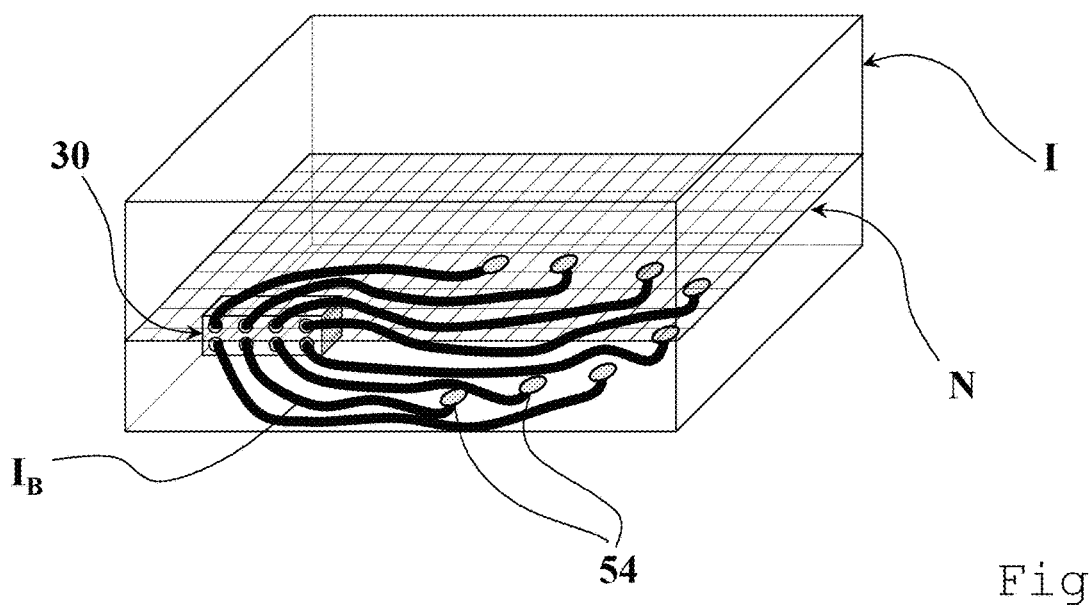
FIG. 5 is a schematic isometric view of an incubator and sampling system according to another example of the present invention.

Turning now to FIG. 5, yet another example is shown in which, instead of a mattress, a net N is provided within the incubator I, elevated and suspended over a bottom surface $I_B$ of the incubator I, allowing the positioning of a monitoring device 30 either between the net N and the bottom surface $I_B$ (as shown) or even outside the incubator I.

It is noted that under this example as well, no channels are required to be formed and the tubes 20 are simply passed through perforations in the net N, allowing sampling of the air within the incubator therethrough.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A system for contactless monitoring of gas levels within an incubator for a neonate, the system comprising:
   at least one gas sampling line having a proximal end exposed to the internal space of the incubator and
   a distal end associated with a monitoring unit for receiving a gas sample obtained from the incubator via the proximal end;
   wherein the system comprises a plurality of sampling channels passing through a mattress located within the incubator and having their proximal openings exposed to the internal space of the incubator at an elevation level of the neonate.

2. A system according to claim 1, wherein the system is configured for monitoring levels of respiratory gases of the neonate located within the incubator, without the need to fit the neonate with a mask, tube or any other mountable/wearable device.

3. A system according to claim 1, wherein said respiratory gases include $CO_2$.

4. A system according to claim 1, wherein the proximal end of the sampling line is located within the incubator at a location, thereby reducing the likelihood of the proximal end being blocked either by the neonate or by any equipment or objects within the incubator.

5. A system according to claim 1, wherein the at least one sampling line comprises a plurality of sampling channels having their respective proximal ends arranged in different locations within the incubator, and configured for obtaining gas samples from different locations within the incubator.

6. A system according to claim 5, wherein the distal ends of the channels are connected by one or both of:
   each distal end being connected to an independent monitoring unit; and
   two or more distal ends being connected to a mutual monitoring unit.

7. A system according to claim 6, wherein, when two or more of the distal ends are connected to the same monitoring unit, the monitoring unit is fitted with a multi-channel processor configured for obtaining samples from a plurality of channels and analyzing them together to output a combined result.

8. A system according to claim 1, wherein the system comprises a support surface installed above the bottom of the incubator, the support surface configured for functioning as a mattress for the neonate.

9. A system according to claim 8, wherein the support surface is elevated above the bottom of the incubator forming a space sufficient for placing monitoring equipment.

10. A system according to claim 8, wherein the support surface is perforated, allowing sampling of $CO_2$ therethrough, without the need for forming holes/channels in a mattress of the incubator.

11. A method for retrofitting an incubator for a neonate with the monitoring system of the first aspect of the invention, said method comprising:
    forming one or more apertures within a mattress or wall of the incubator;
    passing one or more sampling channels through said one or more apertures such that the proximal end is located at the level of the mattress; and
    connecting the distal end of the sampling channel to a monitoring unit configured for monitoring $CO_2$ levels;
    wherein the system comprises a plurality of sampling channels passing through a mattress located within the incubator and having their proximal openings exposed to the internal space of the incubator at the elevation level of the neonate.

12. A method according to claim 11, wherein the plurality of sampling channels have their respective proximal ends arranged in different locations within the incubator, and are configured for obtaining gas samples from different locations within the incubator, and wherein the distal ends of the channels are connected one or both of: each distal end being connected to an independent monitoring unit; and two or more distal ends being connected to a mutual monitoring unit.

13. A system for contactless monitoring of gas levels within an incubator, the system comprising:
    at least one gas sampling line having a proximal end exposed to the internal space of the incubator; and
    a distal end associated with a monitoring unit for receiving a gas sample obtained from the incubator via the proximal end,
    wherein the arrangement includes spreading the proximal openings of the sampling channels across an area of a mattress of the incubator, thereby forming a sampling array.

14. A system according to claim 13, wherein the system is calibrated to identify the location from which sampling port each of the gas samples is obtained.

15. A system according to claim 14, wherein the monitoring unit is configured for forming a special/areal map of the $CO_2$ samples and sample gradients.

16. A system according to claim 13, wherein the array is distributed circumferentially around the approximated position of the head of a neonate when placed on the support surface.

17. A system according to claim 16, wherein the array comprises visual markings configured for indicating to the medical staff where to position the neonate.

18. A system according to claim 17, wherein the array is configured for obtaining samples on all sides of the neonate's head.

* * * * *